US012573477B2

(12) United States Patent (10) Patent No.: US 12,573,477 B2
Chen et al. (45) Date of Patent: Mar. 10, 2026

(54) MOLECULAR STRUCTURE ACQUISITION METHOD AND APPARATUS, ELECTRONIC DEVICE AND STORAGE MEDIUM

(71) Applicant: BEIJING BAIDU NETCOM SCIENCE TECHNOLOGY CO., LTD., Beijing (CN)

(72) Inventors: Zhiyuan Chen, Beijing (CN); Xiaomin Fang, Beijing (CN); Fan Wang, Beijing (CN)

(73) Assignee: BEIJING BAIDU NETCOM SCIENCE TECHNOLOGY CO., LTD., Beijing (CN)

( * ) Notice: Subject to any disclaimer, the term of this patent is extended or adjusted under 35 U.S.C. 154(b) by 1039 days.

(21) Appl. No.: 17/687,809

(22) Filed: Mar. 7, 2022

(65) Prior Publication Data

US 2023/0005572 A1 Jan. 5, 2023

(30) Foreign Application Priority Data

Jun. 30, 2021 (CN) .......................... 202110739352.9

(51) Int. Cl.
*G16C 20/70* (2019.01)
*G06N 20/00* (2019.01)

(52) U.S. Cl.
CPC .............. *G16C 20/70* (2019.02); *G06N 20/00* (2019.01)

(58) Field of Classification Search
CPC ................................. G16C 20/70; G06N 20/00
See application file for complete search history.

(56) References Cited

FOREIGN PATENT DOCUMENTS

| CN | 111063398 | A | 4/2020 |
| CN | 111724867 | A | 9/2020 |
| CN | 112136181 | A | 12/2020 |
| JP | H08512159 | A | 12/1996 |

(Continued)

OTHER PUBLICATIONS

Douguet, Dominique, Etienne Thoreau, and Gérard Grassy. "A genetic algorithm for the automated generation of small organic molecules: drug design using an evolutionary algorithm." Journal of computer-aided molecular design 14.5 (2000): 449-466. (Year: 2000).*

(Continued)

*Primary Examiner* — Kevin W Figueroa
(74) *Attorney, Agent, or Firm* — Brooks Kushman P.C.

(57) ABSTRACT

A molecular structure acquisition method, an electronic device and a storage medium, which relate to the field of artificial intelligence such as deep learning, are disclosed. The method may include: performing, for an initial seed, the following first processing: generating M molecular structures according to the seed, M being a positive integer greater than one; taking the M molecular structures as candidate molecular structures, and selecting some molecular structures from the candidate molecular structures as progeny molecular structures; and performing evolutionary learning on the progeny molecular structures, taking the progeny molecular structures after evolutionary learning as the seed, and repeating the first processing until convergence reaches an optimization objective, and when the convergence reaches the optimization objective, a newly selected molecular structure is taken as a desired molecular structure.

12 Claims, 3 Drawing Sheets

(56) References Cited

FOREIGN PATENT DOCUMENTS

| WO | 2020163860 A1 | 8/2020 |
| WO | 2021080295 A1 | 4/2021 |
| WO | 2021084234 A1 | 5/2021 |

OTHER PUBLICATIONS

Simonovsky, Martin, and Nikos Komodakis. "Graphvae: Towards generation of small graphs using variational autoencoders." International conference on artificial neural networks. Cham: Springer International Publishing, 2018. (Year: 2018).*

Alexandropoulos, Stamatios-Aggelos N., et al. "Multi-objective evolutionary optimization algorithms for machine learning: a recent survey." Approximation and Optimization: Algorithms, Complexity and Applications. Cham: Springer International Publishing, 2019. 35-55. (Year: 2019).*

Liu, Zhiming, Jiliu Zhou, and Su Lai. "New adaptive genetic algorithm based on ranking." Proceedings of the 2003 International Conference on Machine Learning and Cybernetics (IEEE Cat. No. 03EX693). vol. 3. IEEE, 2003. (Year: 2002).*

Zhang, Peng, et al. "A new many-objective evolutionary algorithm based on determinantal point processes." IEEE Transactions on Evolutionary Computation 25.2 (2020): 334-345. (Year: 2020).*

Search Report of Chinese patent application No. 2021107393529 dated Nov. 18, 2021, 2 pages.

Notice of Reasons for Rejection of Japanese application No. JP 2022031687 dated Jun. 6, 2023, 7 pages.

* cited by examiner

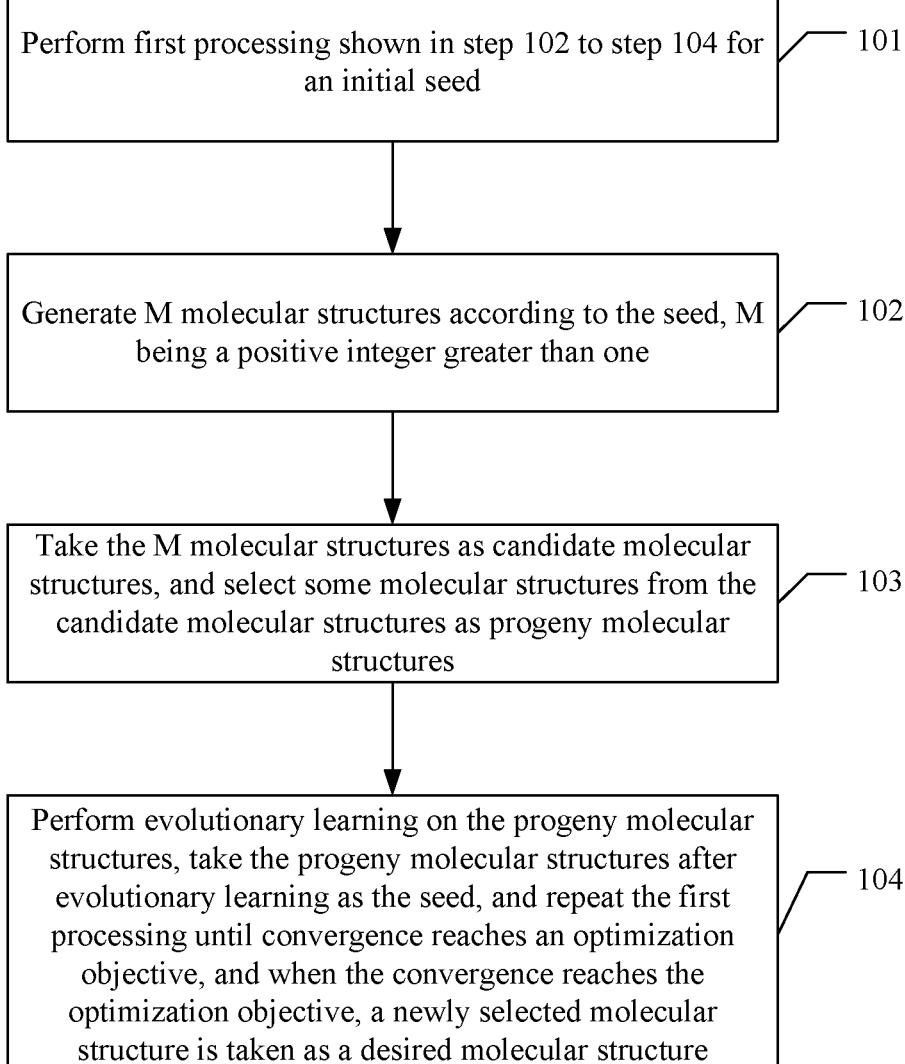

Perform first processing shown in step 102 to step 104 for an initial seed — 101

Generate M molecular structures according to the seed, M being a positive integer greater than one — 102

Take the M molecular structures as candidate molecular structures, and select some molecular structures from the candidate molecular structures as progeny molecular structures — 103

Perform evolutionary learning on the progeny molecular structures, take the progeny molecular structures after evolutionary learning as the seed, and repeat the first processing until convergence reaches an optimization objective, and when the convergence reaches the optimization objective, a newly selected molecular structure is taken as a desired molecular structure — 104

FIG. 1

MOLECULAR STRUCTURE ACQUISITION METHOD AND APPARATUS, ELECTRONIC DEVICE AND STORAGE MEDIUM

CROSS-REFERENCE TO RELATED APPLICATIONS

The present disclosure claims the priority and benefit of Chinese Patent Application No. 202110739352.9, filed on Jun. 30, 2021, entitled "MOLECULAR STRUCTURE ACQUISITION METHOD AND APPARATUS, ELEC-TRONIC DEVICE AND STORAGE MEDIUM." The dis-closure of the above application is incorporated herein by reference in its entirety.

TECHNICAL FIELD

The present disclosure relates to the field of artificial intelligence, in particular to the field of deep learning, and more in particular to a molecular structure acquisition method and apparatus, an electronic device and a storage medium.

BACKGROUND

Molecular structure optimization is an important part of a drug development process, which aims to acquire molecular structures that meet specific properties/requirements.

In a conventional manner, the molecular structure opti-mization involves multidisciplinary intersection of, for example, chemistry, pharmacy and materials science, and molecular structures are generally determined through analysis and experiments of pharmacochemical experts. That is, desired molecular structures are acquired. This manner relies heavily on expert knowledge and requires a lot of biochemical experiments, leading to problems such as high costs and low efficiency.

SUMMARY

The present disclosure provides a molecular structure acquisition method, an electronic device and a storage medium.

A molecular structure acquisition method includes per-forming, for an initial seed, the following first processing: generating M molecular structures according to the seed, M being a positive integer greater than one; taking the M molecular structures as candidate molecular structures, and selecting some molecular structures from the candidate molecular structures as progeny molecular structures; and performing evolutionary learning on the progeny molecular structures, taking the progeny molecular structures after evolutionary learning as the seed, and repeating the first processing until convergence reaches an optimization objec-tive, when the convergence reaches the optimization objec-tive, a newly selected molecular structure is taken as a desired molecular structure.

An electronic device includes at least one processor; and a memory in communication connection with the at least one processor; the memory stores instructions executable by the at least one processor, and the instructions are executed by the at least one processor to enable the at least one processor to perform the method as described above.

A non-transitory computer-readable storage medium stor-ing computer instructions, the computer instructions are configured to cause a computer to perform the method as described above.

It should be understood that the content described in this part is neither intended to identify key or significant features of the embodiments of the present disclosure, nor intended to limit the scope of the present disclosure. Other features of the present disclosure will be made easier to understand through the following description.

BRIEF DESCRIPTION OF THE DRAWINGS

The accompanying drawings are intended to provide a better understanding of the solutions and do not constitute a limitation on the present disclosure. In the drawings, FIG. 1 is a flowchart of a molecular structure acquisition method according to an embodiment of the present disclo-sure;

DETAILED DESCRIPTION

Figure 2:
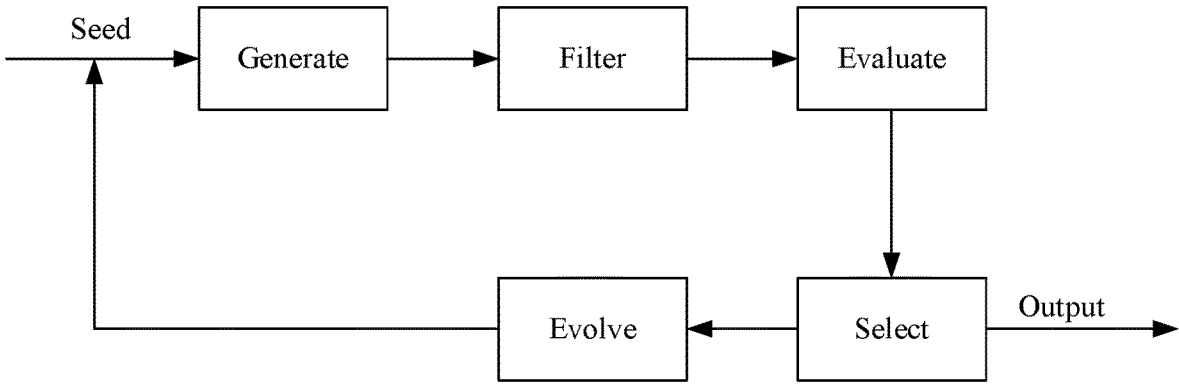
FIG. 2 is a schematic diagram of an overall implementa-tion process of the molecular structure acquisition method according to the present disclosure.

Exemplary embodiments of the present disclosure are illustrated below with reference to the accompanying draw-ings, which include various details of the present disclosure to facilitate understanding and should be considered only as exemplary. Therefore, those of ordinary skill in the art should be aware that various changes and modifications can be made to the embodiments described herein without departing from the scope and spirit of the present disclosure. Similarly, for clarity and simplicity, descriptions of well-known functions and structures are omitted in the following description.

In addition, it shall be understood that the term "and/or" herein is merely an association relationship describing asso-ciated objects, indicating that three relationships may exist. For example, A and/or B indicates that there are three cases of A alone, A and B together, and B alone. In addition, the character "/" herein generally means that associated objects before and after it are in an "or" relationship.

FIG. 1 is a flowchart of a molecular structure acquisition method according to an embodiment of the present disclo-sure. As shown in FIG. 1, the following specific implemen-tations are included.

In step 101, first processing shown in step 102 to step 104 is performed for an initial seed.

In step 102, M molecular structures are generated accord-ing to the seed, M being a positive integer greater than one.

In step 103, the M molecular structures are taken as candidate molecular structures, and some molecular struc-tures are selected from the candidate molecular structures as progeny molecular structures.

In step 104, evolutionary learning is performed on the progeny molecular structures, the progeny molecular struc-tures after evolutionary learning are taken as the seed, and the first processing is repeated until convergence reaches an optimization objective, when the convergence reaches the optimization objective, a newly selected molecular structure is taken as a desired molecular structure.

As may be seen, in the solution according to the above method embodiment, an evolutionary-algorithm-based molecular evolution process is adopted, and a desired molecular structure can be acquired automatically through a series of processing such as cyclic iteration to gradually approach a target for optimization, which reduces implementation costs and improves processing efficiency compared with an existing manner.

There is no restriction on how to acquire the initial seed, which may be randomly generated, for example. The initial seed is an initial molecular structure as a seed. One or more initial seeds may be provided.

M molecular structures may be generated according to the initial seed. M is a positive integer greater than one, of which the specific value may be determined according to an actual requirement. In one embodiment of the present disclosure, the M molecular structures may be generated according to the seed by hidden space (or referred to as implicit space) sampling. A hidden space refers to a data space after raw data is compressed by a neural network, generally with standard normal distribution, so as to facilitate sampling.

There is no restriction on how to generate the M molecular structures. For example, any generation model based on hidden space sampling may be used to generate the M molecular structures by hidden space sampling. Not limited by the generation form, a model structure may be based on, for example, a Variational Auto-Encoder (VAE) or a Flow. A model data structure may be based on, for example, a sequence, a graph, or a 3D spatial structure.

The generated M molecular structures may be directly taken as candidate molecular structures for subsequent processing. In one embodiment of the present disclosure, for the generated M molecular structures, unqualified molecular structures may be filtered out first, and then the remaining molecular structures after the filtering may be taken as the candidate molecular structures for subsequent processing.

There is no restriction on how to filter out the unqualified molecular structures. For example, the unqualified molecular structures may be filtered out using a pre-trained filtering model, or the unqualified molecular structures may be filtered out based on a pre-defined filtering rule.

Through the filtering, the workload of subsequent processing may be reduced, and processing efficiency and accuracy of processing results may be improved.

For the candidate molecular structures, some molecular structures may be selected therefrom as the progeny molecular structures. That is, the molecular structures proceeding to next evolution process are selected.

In one embodiment of the present disclosure, evaluation scores of the candidate molecular structures may be acquired respectively, and the progeny molecular structures are selected according to the evaluation scores.

In order to acquire the evaluation scores, in one embodiment of the present disclosure, for each of the candidate molecular structures, the following processing may be performed: acquiring P score(s) of the candidate molecular structure, P being a positive integer, different scores corresponding to different optimization objectives; when P is equal to one, taking the scores as the evaluation score of the candidate molecular structure; and when P is greater than one, integrating the P scores to determine the evaluation score of the candidate molecular structure.

The evolution process described in the present disclosure may be embedded into any computable optimization objective. That is, any computable objective may be theoretically optimized without being limited to optimization scenarios. One or more optimization objectives may be provided.

For example, the value of P may be 2. That is, 2 optimization objectives may be provided. Moreover, it is assumed that, for each candidate molecular structure, a score may be determined by using a molecular activity prediction model and an oil-water distribution coefficient prediction model respectively. That is, 2 scores may be acquired respectively for each candidate molecular structure. An optimization scenario corresponding to the molecular activity prediction model is molecular structure optimization for a target, and an optimization scenario corresponding to the oil-water distribution coefficient prediction model is optimization for results of hydrophilicity or hydrophobicity of molecules.

Generally, numbers and types of scores corresponding to different candidate molecular structures are the same. For example, 1 score of the different candidate molecular structures may be acquired respectively by using the molecular activity prediction model, or 2 scores of the different candidate molecular structures may be acquired respectively by using the molecular activity prediction model and the oil-water distribution coefficient prediction model.

For any candidate molecular structure, when P is equal to one, the score may be directly taken as the evaluation score of the candidate molecular structure, and when P is greater than one, the P scores may be integrated to determine the evaluation score of the candidate molecular structure. For example, the P scores may be weighted and added, and calculation results may be taken as the evaluation score of the candidate molecular structure. Weights corresponding to different scores may be the same or different.

For any candidate molecular structure, the evaluation score thereof refers to an adaptability score of the molecular structure in the evolution process.

By means of the evaluation scores, the progeny molecular structures can be screened accurately and efficiently, which lays a good foundation for subsequent processing.

In one embodiment of the present disclosure, the progeny molecular structures may be selected according to the evaluation scores in the following specific manners.

1) The candidate molecular structures are sorted in descending order of the evaluation scores, and the molecular structures in the first N positions after sorting are taken as the progeny molecular structures. N is a positive integer and less than a number of the candidate molecular structures.

2) The progeny molecular structures are selected from the candidate molecular structures according to the evaluation scores by a determinant point process (DPP).

In the manner 1), the N molecular structures with the highest evaluation scores are selected as the progeny molecular structures from the perspective of elite selection. In the manner 2), a subset considering both evaluation scores and molecular diversity may be selected from the candidate molecular structures by the DPP, and molecular structures in the subset are taken as the progeny molecular structures. A specific manner may be determined according to an actual requirement, which is very flexible and convenient. Specific implementation of the DPP is a prior art.

Further, evolutionary learning may be performed on the progeny molecular structures, so that the molecular structures mutate in anticipation of a higher evaluation score in next evolution process.

There is no restriction on how to perform the evolutionary learning. For example, the evolutionary learning may be realized by a genetic algorithm or an evolutionary strategy.

Further, the progeny molecular structure after the evolutionary learning may be taken as the seed, and the first processing is repeated until convergence reaches an optimization objective.

In one embodiment of the present disclosure, a hidden space corresponding to the progeny molecular structures after evolutionary learning may also be regularized, and then the first processing is repeated.

Through the regularization, a distance between a hidden space vector and a spatial origin may be shortened, preventing excessive deviation of the hidden space vector from a normal molecular data distribution center, so that the optimized molecular structure more similar to drug molecules, so as to prevent excessively strange molecular structures. How to perform the regularization is a prior art.

When the convergence reaches the optimization objective, a newly selected molecular structure may be taken as a desired molecular structure, that is, as a final acquired molecular structure.

Based on the above introduction, FIG. 2 is a schematic diagram of an overall implementation process of the molecular structure acquisition method according to the present disclosure.

As shown in FIG. 2, a generation operation may be performed for the initial seed. That is, M molecular structures are generated. M is a positive integer greater than one. For example, the M molecular structures may be generated according to the seed by hidden space sampling.

As shown in FIG. 2, then, a filtering operation may be performed. That is, unqualified molecular structures may be filtered out from the generated molecular structures, and the remaining molecular structures after the filtering are taken as the candidate molecular structures.

As shown in FIG. 2, then, an evaluation operation may be performed. That is, evaluation scores of the candidate molecular structures are acquired respectively. For example, for each of the candidate molecular structures, the following processing may be performed: acquiring P scores of the candidate molecular structure, P being a positive integer, different scores corresponding to different optimization objectives; when P is equal to one, taking the scores as the evaluation score of the candidate molecular structure; and when P is greater than one, integrating the P scores to determine the evaluation score of the candidate molecular structure.

As shown in FIG. 2, then, a selection operation may be performed. That is, some molecular structures are selected, according to the evaluation scores, from the candidate molecular structures as progeny molecular structures. For example, the candidate molecular structures may be sorted in descending order of the evaluation scores, and the molecular structures in the first N positions after sorting are taken as the progeny molecular structures. N is a positive integer and less than a number of the candidate molecular structures. Alternatively, the progeny molecular structures may be selected from the candidate molecular structures according to the evaluation scores by a DPP.

As shown in FIG. 2, then, an evolution operation may be performed. That is, evolutionary learning may be performed on the progeny molecular structures. Further, the progeny molecular structures after evolutionary learning may be taken as the seed, and the above processing is repeated until convergence reaches an optimization objective. When the convergence reaches the optimization objective, a newly selected molecular structure may be outputted as a desired molecular structure.

The specific implementation of the process shown in FIG. 2 may be obtained with reference to the above related description, and is not described in detail here.

In conclusion, the solutions according to the present disclosure can automatically realize molecular structure optimization, and may take into account the diversity of molecular structure and drug-like properties, etc. In addition, other models in a drug research and development platform can be effectively and flexibly combined, independent of forms of the combined models.

It is to be noted that for the sake of simplicity, the method embodiments described above are described as a combination of a series of actions. However, those of ordinary skill in the art should understand that the present disclosure is not limited by the order of action described. Therefore, according to the present disclosure, some steps may be performed in another order or at the same time. Secondly, those of ordinary skill in the art should also know that the embodiments described in the specification are preferred embodiments and the actions and modules involved are not necessary to the present disclosure.

The above is the introduction to the method embodiments. The following is a further illustration of the solutions according to the present disclosure through apparatus embodiments.

Figure 3:
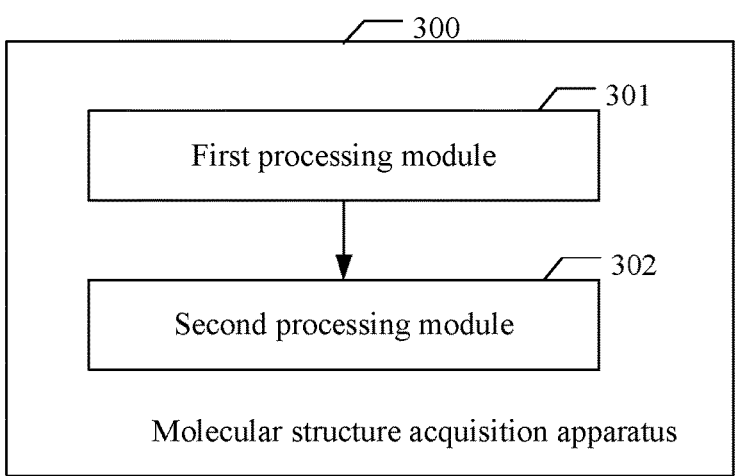
FIG. 3 is a schematic diagram of composition of a molecular structure acquisition apparatus 300 according to an embodiment of the present disclosure.

FIG. 3 is a schematic diagram of composition of a molecular structure acquisition apparatus 300 according to an embodiment of the present disclosure. As shown in FIG. 3, the apparatus includes: a first processing module 301 and a second processing module 302.

The first processing module 301 is configured to acquire an initial seed and send the initial seed to the second processing module 302.

The second processing module 302 is configured to perform, for the seed, the following first processing: generating M molecular structures according to the seed, M being a positive integer greater than one; taking the M molecular structures as candidate molecular structures, and selecting some molecular structures from the candidate molecular structures as progeny molecular structures; and performing evolutionary learning on the progeny molecular structures, taking the progeny molecular structures after evolutionary learning as the seed, and repeating the first processing until convergence reaches an optimization objective, when the convergence reaches the optimization objective, a newly selected molecular structure is taken as a desired molecular structure.

In one embodiment of the present disclosure, the second processing module 302 may generate the M molecular structures according to the acquired seed.

There is no restriction on how to generate the M molecular structures. For example, any generation model based on hidden space sampling may be used to generate the M molecular structures by hidden space sampling. Not limited by the generation form, a model structure may be based on, for example, a VAE or a Flow. A model data structure may be based on, for example, a sequence, a graph, or a 3D spatial structure.

The second processing module 302 may directly take the generated M molecular structures as candidate molecular structures for subsequent processing. In one embodiment of the present disclosure, for the generated M molecular structures, the second processing module 302 may first filter out unqualified molecular structures, and then take the remaining molecular structures after the filtering as the candidate molecular structures for subsequent processing.

There is no restriction on how to filter out the unqualified molecular structures. For example, the unqualified molecular structures may be filtered out using a pre-trained filtering model, or the unqualified molecular structures may be filtered out based on a pre-defined filtering rule.

For the candidate molecular structures, the second processing module 302 may select some molecular structures therefrom as the progeny molecular structures. That is, the molecular structures proceeding to next evolution process are selected.

In one embodiment of the present disclosure, the second processing module 302 may acquire evaluation scores of the candidate molecular structures respectively, and select the progeny molecular structures according to the evaluation scores.

In order to acquire the evaluation scores, in one embodiment of the present disclosure, for each of the candidate molecular structures, the second processing module 302 may perform following processing: acquiring P scores of the candidate molecular structure, P being a positive integer, different scores corresponding to different optimization objectives; when P is equal to one, taking the scores as the evaluation score of the candidate molecular structure; and when P is greater than one, integrating the P scores to determine the evaluation score of the candidate molecular structure.

The evolution process described in the present disclosure may be embedded into any computable optimization objective. That is, any computable objective may be theoretically optimized without being limited to optimization scenarios. One or more optimization objectives may be provided.

For example, the value of P may be 2. That is, 2 optimization objectives may be provided. Moreover, it is assumed that, for each candidate molecular structure, a score may be determined by using a molecular activity prediction model and an oil-water distribution coefficient prediction model respectively. That is, 2 scores may be acquired respectively for each candidate molecular structure. An optimization scenario corresponding to the molecular activity prediction model is molecular structure optimization for a target, and an optimization scenario corresponding to the oil-water distribution coefficient prediction model is optimization for results of hydrophilicity or hydrophobicity of molecules.

For any candidate molecular structure, when P is equal to one, the score may be directly taken as the evaluation score of the candidate molecular structure, and when P is greater than one, the P scores may be integrated to determine the evaluation score of the candidate molecular structure. For example, the P scores may be weighted and added, and calculation results may be taken as the evaluation score of the candidate molecular structure. Weights corresponding to different scores may be the same or different.

In one embodiment of the present disclosure, the second processing module 302 may sort the candidate molecular structures in descending order of the evaluation scores, and take the molecular structures in the first N positions after sorting as the progeny molecular structures. N is a positive integer and less than a number of the candidate molecular structures. Alternatively, the second processing module 302 may select the progeny molecular structures from the candidate molecular structures according to the evaluation scores by a DPP.

Further, the second processing module 302 may perform evolutionary learning on the progeny molecular structures, so that the molecular structures mutate in anticipation of a higher evaluation score in next evolution process.

There is no restriction on how to perform the evolutionary learning. For example, the evolutionary learning may be realized by a genetic algorithm or an evolutionary strategy.

Further, the second processing module 302 may take the progeny molecular structure after the evolutionary learning as the seed, and repeat the first processing until convergence reaches an optimization objective.

In one embodiment of the present disclosure, the second processing module 302 may further regularize a hidden space corresponding to the progeny molecular structures after evolutionary learning, and then repeat the first processing.

When the convergence reaches the optimization objective, the second processing module 302 may take a newly selected molecular structure as a desired molecular structure, that is, as a final acquired molecular structure.

The specific workflow of the apparatus embodiment shown in FIG. 3 can be obtained with reference to the related description in the above method embodiment and is not repeated.

In conclusion, by use of the solution of the apparatus embodiment of the present disclosure, a desired molecular structure can be automatically acquired through a series of processing such as cyclic iteration, so as to realize molecular structure optimization, thereby reducing implementation costs and improving processing efficiency compared with an existing manner.

The solutions described in the present disclosure may be applied to the field of artificial intelligence, and in particular, to the field of, for example, deep learning. Artificial intelligence is a discipline that studies how to make computers simulate certain thinking processes and intelligent behaviors (such as learning, reasoning, thinking and planning) of human beings, which includes hardware technologies and software technologies. The artificial intelligence hardware technologies generally include sensors, dedicated artificial intelligence chips, cloud computing, distributed storage, big data processing and other technologies. The artificial intelligence software technologies mainly include a computer vision technology, a speech recognition technology, a natural language processing technology, machine learning/deep learning, a big data processing technology, a knowledge graph technology and other major directions.

According to embodiments of the present disclosure, the present disclosure further provides an electronic device, a readable storage medium and a computer program product.

Figure 4:
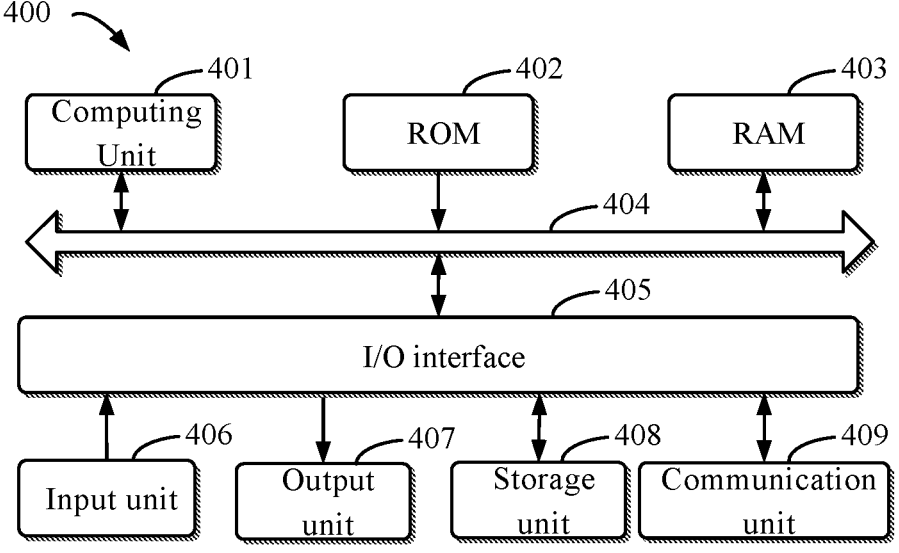
FIG. 4 is a schematic block diagram of an exemplary electronic device 400 that can be configured to implement embodiments of the present disclosure.

FIG. 4 is a schematic block diagram of an exemplary electronic device 400 that can be configured to implement embodiments of the present disclosure. The electronic device is intended to represent various forms of digital computers, such as laptops, desktops, workbenches, personal digital assistants, servers, blade servers, mainframe computers and other suitable computers. The electronic device may further represent various forms of mobile devices, such as personal digital assistants, cellular phones, smart phones, wearable devices and other similar computing devices. The components, their connections and relationships, and their functions shown herein are examples only, and are not intended to limit the implementation of the present disclosure as described and/or required herein.

As shown in FIG. 4, the device 400 includes a computing unit 401, which may perform various suitable actions and processing according to a computer program stored in a read-only memory (ROM) 402 or a computer program loaded from a storage unit 408 into a random access memory (RAM) 403. The RAM 403 may also store various programs and data required to operate the device 400. The computing unit 401, the ROM 402 and the RAM 403 are connected to one another by a bus 404. An input/output (I/O) interface 405 may also be connected to the bus 404.

A plurality of components in the device 400 are connected to the I/O interface 405, including an input unit 406, such as a keyboard and a mouse; an output unit 407, such as various displays and speakers; a storage unit 408, such as disks and discs; and a communication unit 409, such as a network card, a modem and a wireless communication transceiver. The communication unit 409 allows the device 400 to exchange information/data with other devices over computer networks such as the Internet and/or various telecommunications networks.

The computing unit 401 may be a variety of general-purpose and/or special-purpose processing components with processing and computing capabilities. Some examples of the computing unit 401 include, but are not limited to, a central processing unit (CPU), a graphics processing unit (GPU), various artificial intelligence (AI) computing chips, various computing units that run machine learning model algorithms, a digital signal processor (DSP), and any appropriate processor, controller or microcontroller, etc. The computing unit 401 performs the methods and processing described above, such as the methods described in the present disclosure. For example, in some embodiments, the method described in the present disclosure may be implemented as a computer software program that is tangibly embodied in a machine-readable medium, such as a storage unit 408. In some embodiments, part or all of a computer program may be loaded and/or installed on the device 400 via the ROM 402 and/or the communication unit 409. One or more steps of the method described in the present disclosure may be performed when the computer program is loaded into the RAM 403 and executed by the computing unit 401. Alternatively, in other embodiments, the computing unit 401 may be configured to perform the methods described in the present disclosure by any other appropriate means (for example, by means of firmware).

Various implementations of the systems and technologies disclosed herein can be realized in a digital electronic circuit system, an integrated circuit system, a field programmable gate array (FPGA), an application-specific integrated circuit (ASIC), an application-specific standard product (ASSP), a system on chip (SOC), a load programmable logic device (CPLD), computer hardware, firmware, software, and/or combinations thereof. Such implementations may include implementation in one or more computer programs that are executable and/or interpretable on a programmable system including at least one programmable processor, which can be special or general purpose, coupled to receive data and instructions from a storage system, at least one input apparatus, and at least one output apparatus, and to transmit data and instructions to the storage system, the at least one input apparatus, and the at least one output apparatus.

Program codes configured to implement the methods in the present disclosure may be written in any combination of one or more programming languages. Such program codes may be supplied to a processor or controller of a general-purpose computer, a special-purpose computer, or another programmable data processing apparatus to enable the function/operation specified in the flowchart and/or block diagram to be implemented when the program codes are executed by the processor or controller. The program codes may be executed entirely on a machine, partially on a machine, partially on a machine and partially on a remote machine as a stand-alone package, or entirely on a remote machine or a server.

In the context of the present disclosure, machine-readable media may be tangible media which may include or store programs for use by or in conjunction with an instruction execution system, apparatus or device. The machine-readable media may be machine-readable signal media or machine-readable storage media. The machine-readable media may include, but are not limited to, electronic, magnetic, optical, electromagnetic, infrared, or semiconductor systems, apparatuses or devices, or any suitable combinations thereof. More specific examples of machine-readable storage media may include electrical connections based on one or more wires, a portable computer disk, a hard disk, a random access memory (RAM), a read-only memory (ROM), an erasable programmable read only memory (EPROM or flash memory), an optical fiber, a compact disk read only memory (CD-ROM), an optical storage device, a magnetic storage device, or any suitable combination thereof.

To provide interaction with a user, the systems and technologies described here can be implemented on a computer. The computer has: a display apparatus (e.g., a cathode-ray tube (CRT) or a liquid crystal display (LCD) monitor) for displaying information to the user; and a keyboard and a pointing apparatus (e.g., a mouse or trackball) through which the user may provide input for the computer. Other kinds of apparatuses may also be configured to provide interaction with the user. For example, a feedback provided for the user may be any form of sensory feedback (e.g., visual, auditory, or tactile feedback); and input from the user may be received in any form (including sound input, voice input, or tactile input).

The systems and technologies described herein can be implemented in a computing system including background components (e.g., as a data server), or a computing system including middleware components (e.g., an application server), or a computing system including front-end components (e.g., a user computer with a graphical user interface or web browser through which the user can interact with the implementation mode of the systems and technologies described here), or a computing system including any combination of such background components, middleware components or front-end components. The components of the system can be connected to each other through any form or medium of digital data communication (e.g., a communication network). Examples of the communication network include: a local area network (LAN), a wide area network (WAN) and the Internet.

The computer system may include a client and a server. The client and the server are generally far away from each other and generally interact via the communication network. A relationship between the client and the server is generated through computer programs that run on a corresponding computer and have a client-server relationship with each other. The server may be a cloud server, also known as a cloud computing server or cloud host, which is a host product in the cloud computing service system to solve the problems of difficult management and weak business scalability in the traditional physical host and a virtual private server (VPS). The server may also be a distributed system server, or a server combined with blockchain. Cloud computing refers to a technical system that is connected to an elastic and scalable shared physical or virtual resource pool over a network and may deploy and manage resources on demand and in a self-service manner. The resources include servers, operating systems, networks, software, applications, storage devices, and so on. Through a cloud computing technology, efficient and powerful data processing capabilities can be provided for technical applications, such as artificial intelligence and blockchain, and model training.

It should be understood that the steps can be reordered, added, or deleted using the various forms of processes shown above. For example, the steps described in the present disclosure may be executed in parallel or sequentially or in different sequences, provided that desired results of the technical solutions disclosed in the present disclosure are achieved, which is not limited herein.

The above specific implementations do not limit the extent of protection of the present disclosure. Those skilled in the art should understand that various modifications, combinations, sub-combinations, and replacements can be made according to design requirements and other factors. Any modifications, equivalent substitutions and improvements made within the spirit and principle of the present disclosure all should be included in the extent of protection of the present disclosure.

What is claimed is:

1. A molecular structure acquisition method, comprising:
performing, for an initial seed, the following first processing:
generating M molecular structures according to the seed by hidden space sampling, M being a positive integer greater than one;
taking the M molecular structures as candidate molecular structures, acquiring evaluation scores of the candidate molecular structures respectively; and selecting some molecular structures from the candidate molecular structures as progeny molecular structures according to the evaluation scores;
wherein acquiring evaluation scores of the candidate molecular structures respectively comprises, for each of the candidate molecular structures: acquiring P score (s) of the candidate molecular structure, P being a positive integer, different scores corresponding to different optimization objectives; when P is equal to one, taking the score as the evaluation score of the candidate molecular structure; and when P is greater than one, integrating the P scores to determine the evaluation score of the candidate molecular structure;
performing evolutionary learning on the progeny molecular structures, taking the progeny molecular structures after evolutionary learning as the seed, and repeating the first processing until convergence reaches an optimization objective, wherein, when the convergence reaches the optimization objective, a newly selected molecular structure is taken as a desired molecular structure.

2. The method according to claim 1, further comprising:
filtering out unqualified molecular structures from the molecular structures generated, and taking remaining molecular structures after the filtering as the candidate molecular structures.

3. The method according to claim 1, wherein selecting the progeny molecular structures according to the evaluation scores comprises:
sorting the candidate molecular structures in descending order of their evaluation scores, and taking the molecular structures in the first N positions after sorting as the progeny molecular structures, N being a positive integer and less than a number of the candidate molecular structures.

4. The method according to claim 1, wherein selecting the progeny molecular structures according to the evaluation scores comprises:
selecting the progeny molecular structures from the candidate molecular structures according to the evaluation scores by a determinant point process (DPP).

5. The method according to claim 1, further comprising: regularizing a hidden space corresponding to the progeny molecular structures after the evolutionary learning.

6. An electronic device, comprising:
at least one processor; and
a memory in communication connection with the at least one processor; wherein
the memory stores instructions executable by the at least one processor, and the instructions are executed by the at least one processor to enable the at least one processor to perform a molecular structure acquisition method, which comprises:
performing, for an initial seed, the following first processing:
generating M molecular structures according to the seed by hidden space sampling, M being a positive integer greater than one;
taking the M molecular structures as candidate molecular structures, acquiring evaluation scores of the candidate molecular structures respectively; and selecting some molecular structures from the candidate molecular structures as progeny molecular structures according to the evaluation scores;
wherein acquiring evaluation scores of the candidate molecular structures respectively comprises, for each of the candidate molecular structures: acquiring P score(s) of the candidate molecular structure, P being a positive integer, different scores corresponding to different optimization objectives; when P is equal to one, taking the score as the evaluation score of the candidate molecular structure; and when P is greater than one, integrating the P scores to determine the evaluation score of the candidate molecular structure;
performing evolutionary learning on the progeny molecular structures, taking the progeny molecular structures after evolutionary learning as the seed, and repeating the first processing until convergence reaches an optimization objective, wherein, when the convergence reaches the optimization objective, a newly selected molecular structure is taken as a desired molecular structure.

7. The electronic device according to claim 6, wherein the method further comprises:
filtering out unqualified molecular structures from the molecular structures generated, and taking remaining molecular structures after the filtering as the candidate molecular structures.

8. The electronic device according to claim 6, wherein selecting the progeny molecular structures according to the evaluation scores comprises:
sorting the candidate molecular structures in descending order of their evaluation scores, and taking the molecular structures in the first N positions after sorting as the progeny molecular structures, N being a positive integer and less than a number of the candidate molecular structures.

9. The electronic device according to claim 6, wherein selecting the progeny molecular structures according to the evaluation scores comprises:
selecting the progeny molecular structures from the candidate molecular structures according to the evaluation scores by a determinant point process (DPP).

10. The electronic device according to claim 6, wherein the method further comprises: regularizing a hidden space corresponding to the progeny molecular structures after the evolutionary learning.

11. A non-transitory computer-readable storage medium storing computer instructions, wherein the computer instructions are configured to cause a computer to perform a molecular structure acquisition method, which comprises:

performing, for an initial seed, the following first processing:

generating M molecular structures according to the seed by hidden space sampling, M being a positive integer greater than one;

taking the M molecular structures as candidate molecular structures, acquiring evaluation scores of the candidate molecular structures respectively; and selecting some molecular structures from the candidate molecular structures as progeny molecular structures according to the evaluation scores;

wherein acquiring evaluation scores of the candidate molecular structures respectively comprises, for each of the candidate molecular structures: acquiring P score(s) of the candidate molecular structure, P being a positive integer, different scores corresponding to different optimization objectives; when P is equal to one, taking the score as the evaluation score of the candidate molecular structure; and when P is greater than one, integrating the P scores to determine the evaluation score of the candidate molecular structure;

performing evolutionary learning on the progeny molecular structures, taking the progeny molecular structures after evolutionary learning as the seed, and repeating the first processing until convergence reaches an optimization objective, wherein, when the convergence reaches the optimization objective, a newly selected molecular structure is taken as a desired molecular structure.

12. The non-transitory computer-readable storage medium according to claim 11, wherein the method further comprises:

filtering out unqualified molecular structures from the molecular structures generated, and taking remaining molecular structures after the filtering as the candidate molecular structures.

* * * * *